(12) United States Patent
Johnston et al.

(10) Patent No.: US 6,293,163 B1
(45) Date of Patent: Sep. 25, 2001

(54) FLUID SAMPLING TOOL

(75) Inventors: Roger G. Johnston, Los Alamos; Anthony R. E. Garcia, Espanola; Ronald K. Martinez, Santa Cruz, all of NM (US)

(73) Assignee: The Regents of the University of California, Los Alamos, NM (US)

(*) Notice: Subject to any disclaimer, the term of this patent is extended or adjusted under 35 U.S.C. 154(b) by 0 days.

(21) Appl. No.: 09/281,759

(22) Filed: Mar. 30, 1999

Related U.S. Application Data

(60) Provisional application No. 60/080,059, filed on Mar. 31, 1998.

(51) Int. Cl.[7] ............... G01N 01/10; G01N 01/00; G01N 01/12
(52) U.S. Cl. .............. 73/864.74; 73/863; 73/864.63
(58) Field of Search ................. 73/863, 864.74, 73/864.63

(56) References Cited

U.S. PATENT DOCUMENTS

| | | | |
|---|---|---|---|
| 4,350,052 | 9/1982 | Kendall | 73/863.86 |
| 5,341,692 * | 8/1994 | Sher et al. | 73/864.63 |
| 5,558,140 | 9/1996 | Clark, II | 141/98 |
| 5,704,383 | 1/1998 | Kammeraad | 137/15 |
| 5,907,110 * | 5/1999 | Garcia et al. | 73/864.74 |

* cited by examiner

*Primary Examiner*—Daniel S. Larkin
*Assistant Examiner*—Katina Wilson
(74) *Attorney, Agent, or Firm*—Samuel L. Borkowsky

(57) ABSTRACT

The invention includes a rotatable tool for collecting fluid through the wall of a container. The tool includes a fluid collection section with a cylindrical shank having an end portion for drilling a hole in the container wall when the tool is rotated, and a threaded portion for tapping the hole in the container wall. A passageway in the shank in communication with at least one radial inlet hole in the drilling end and an opening at the end of the shank is adapted to receive fluid from the container. The tool also includes a cylindrical chamber affixed to the end of the shank opposite to the drilling portion thereof for receiving and storing fluid passing through the passageway. The tool also includes a flexible, deformable gasket that provides a fluid-tight chamber to confine kerf generated during the drilling and tapping of the hole. The invention also includes a fluid extractor section for extracting fluid samples from the fluid collecting section.

8 Claims, 6 Drawing Sheets

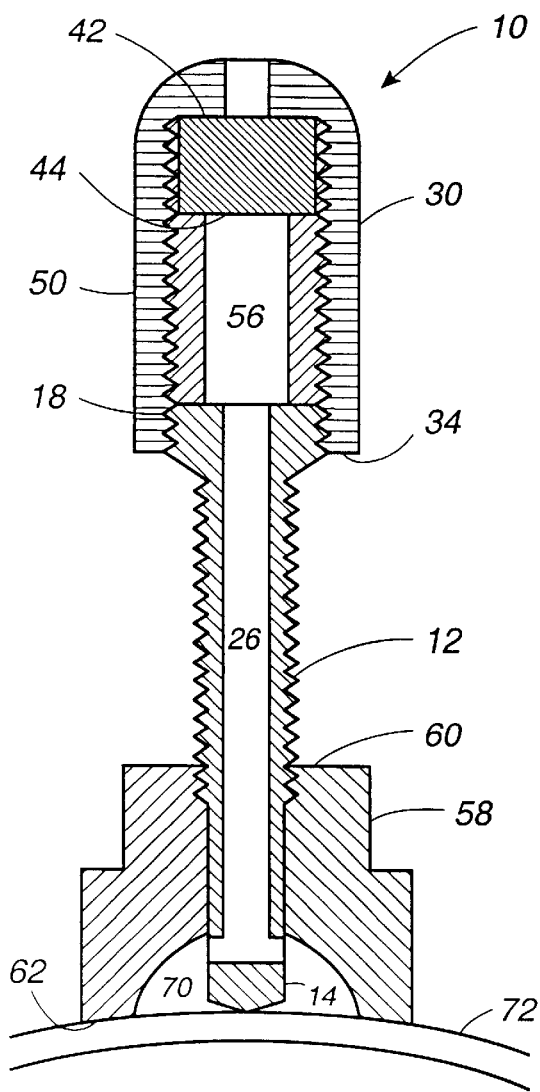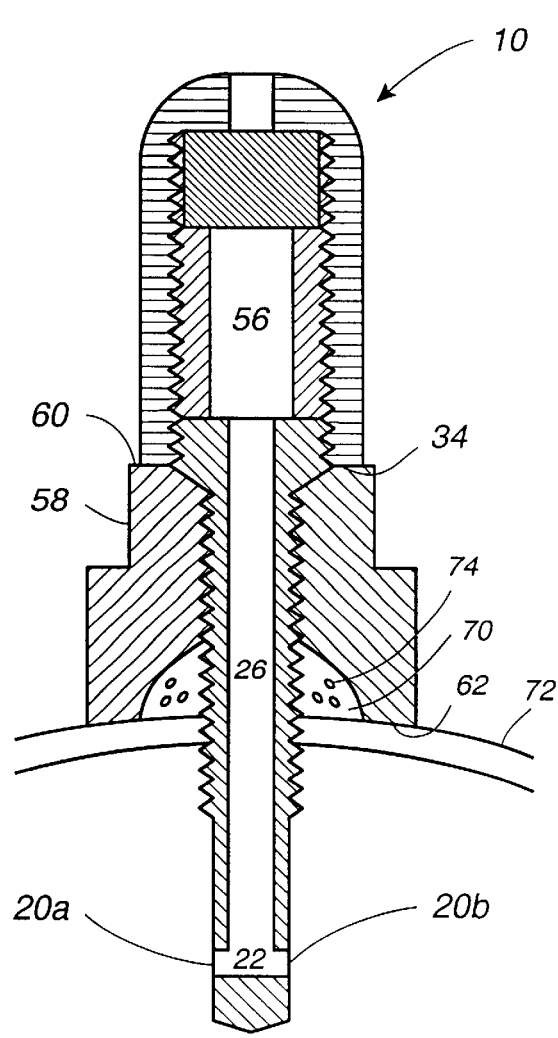
Fig. 2
Fig. 3

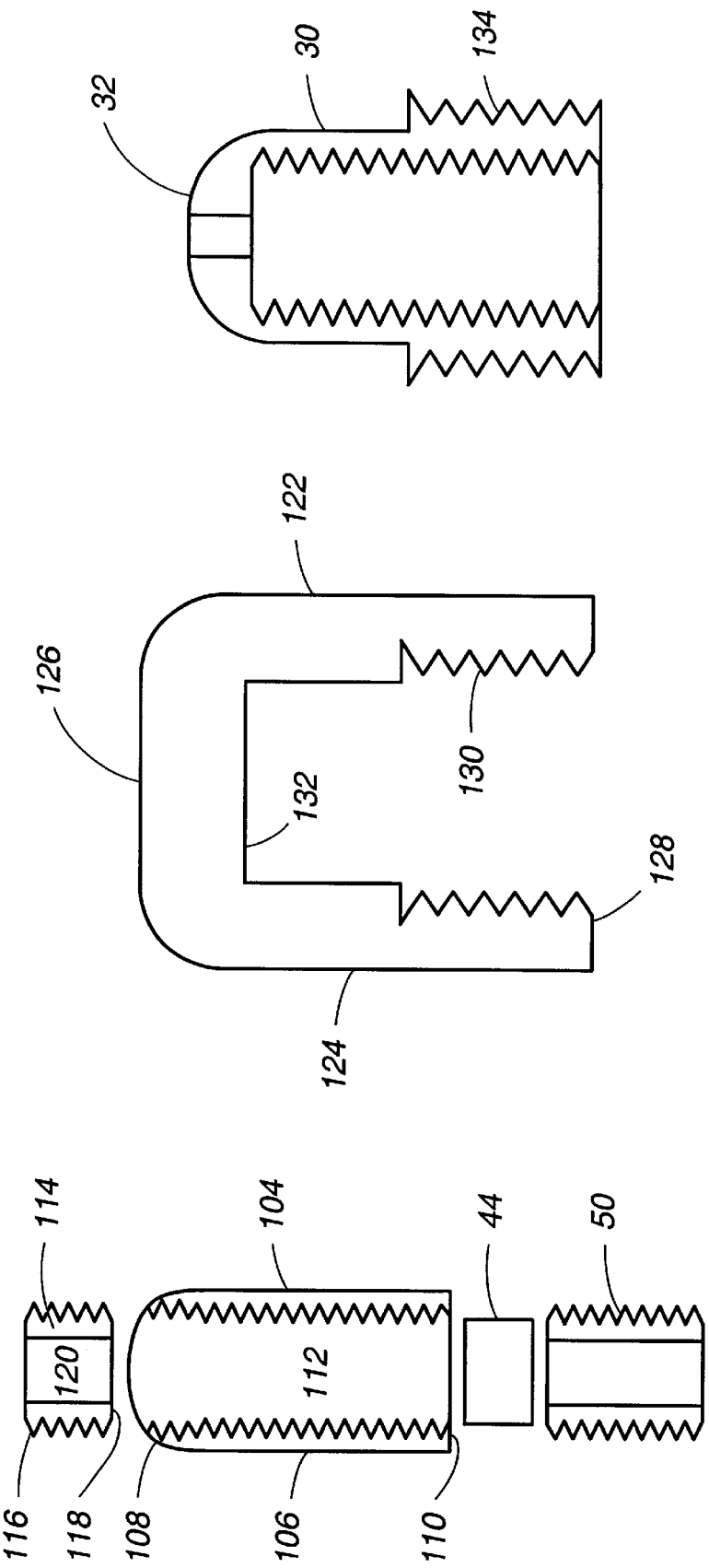

FLUID SAMPLING TOOL

The present invention relates generally to chemical sampling tools and, more particularly, to tools which allow the withdrawal of a fluid sample from a sealed container without exposing the user or the environment to the container fluid. This application claims the benefit under U. S. C. 119(e) of U. S. Provisional Application SN 60/080,058 filed Mar. 31, 1998.

This invention was made with government support under Contract No. W-7405-ENG-36 awarded by the U.S. Department of Energy to The Regents of the University of California. The government has certain rights in the invention.

FIELD OF THE INVENTION

BACKGROUND OF THE INVENTION

The treatment and disposal of stored hazardous waste is a challenge. Prior to treatment and/or disposal, it is often necessary to store waste in a container. One possible reason for storing waste is that, at present, there may be no effective procedure for treating it. Another reason may be that the waste is not adequately characterized to make a determination of the appropriate treatment procedure. Thus, situations have arisen where large quantities of untreated waste remain stored in containers and await treatment.

A typical waste storage container for a liquid waste is a metal drum having a lid. Waste is poured into the container, and a lid is sealed to the container to prevent the waste from escaping. When the time comes to dispose of the waste, it may be necessary to determine its composition. Since an analysis of the waste composition from a sealed container may be necessary before an appropriate treatment and disposal procedure is implemented, a device for extracting a sample of waste from a sealed container is required.

Other types of sealed containers, which may hold hazardous materials, would similarly require a device for extracting a sample of their contents to determine an effective procedure for treatment and/or disposal. Munitions, which may contain dangerous chemical weapons, fall in this category. It may also be important to obtain a fluid sample onsite, and to obtain the sample quickly, effectively, and safely. Importantly, during a sampling procedure, the user must avoid exposure to the material being sampled while obtaining a sample and while transporting the sample to a site for analysis. Devices which allow one to tap and/or sample the fluid contents of containers are known.

In U.S. Pat. No. 4,350,052 entitled "Apparatus and Method for Tapping and Extracting Oil Samples From an Underground High Pressure Pipe-Type Transmission Cable System" by R. W. Kendall which issued Sep. 21, 1982, an apparatus and method for extracting oil from high-voltage cables is described. After removing any covering from the outer surface of the cable, the nipple of the apparatus is welded to the pipe, forming a chamber. After drilling a hole in the cable and withdrawing the drill bit, the chamber fills with oil from the cable. A ball valve is installed to control the flow of oil out of the cable.

In U.S. Pat. No. 5,704,383 by D. A. Kammeraad et al. entitled "Tool and Method For Removing Fluid From Container" which issued Jan. 6, 1998, a tool for tapping and removing fluid from a container is described. The tool bit is configured to bore a hole through a container wall. The shank has a frustoconically-shaped, threaded outer surface which sealingly engages the wall as the shank is advanced into the container. Opposing inlets in the bit communicate with an internal passageway within the shank to allow fluid from a container to enter the tool via the inlets and move into the passageway within the shank. An assembly attached to the shank houses a valve piston which prevents fluid in the shank passageway from escaping. A fluid collection unit can be attached to the valve assembly to obtain fluid samples. FIG. 5 of the '383 patent shows the tool fully engaged with the container wall. As FIG. 5 shows, formation of a seal between the sealing surface and the container wall results in deformation of the container wall. Furthermore, advancement of the frustoconically-shaped shank into the container wall increases the borehole size as the shank is advanced into the wall.

In U.S. Pat. No. 5,558,140 by J. E. Clark II entitled "Device For Draining Fluid From a Container" which issued Sep. 24, 1996, a fluid draining device for removing engine oil is described. The device has a threaded screw with a sharpened puncturing tip and an internal fluid channel with at least one opening just behind the tip. It also has a threaded screw guide connected to a strap, which can be wrapped around a container and tightened. An opening in the strap coaxial with the bore of the screw guide allows the screw to pass through the strap. An optional sealing material having an opening coaxial with the strap opening may be placed between the clamp means and the container wall to assist in forming a leak proof seal.

A portable tool for sampling fluid from a sealed container while preventing exposure to the contents is clearly desirable.

Therefore, an object of the invention is to provide a portable tool for collecting fluid from a sealed container without exposure of the sampler to the fluid.

Another object of the invention is to provide a fluid collecting tool that can be drilled into a sealed container without exposure of the user to wall shavings created while drilling.

A further object of the invention is to provide a fluid collecting tool from which a fluid sample or multiple fluid samples can be easily and rapidly withdrawn from sealed containers.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein the rotatable tool for collecting fluid through the wall of a container hereof may include a cylindrical shank having a portion at one end of the shank that is adapted for drilling a hole in the container wall. The shank also has a threaded portion for tapping the hole in the container wall drilled by the drilling portion and for advancing the shank into the container when the shank is rotated. The shank also has an axis, an inner passageway along the axis in communication with at least one radial inlet hole in the drilling portion, and an opening at the end of the shank opposite the drilling portion. When the drilling portion of the shank enters the container, fluid from the container flows into the radial inlet or inlets, and into the passageway. The invention also includes a cylindrical chamber affixed to the end of the shank opposite to the drilling portion for receiving and storing fluid passing through the passageway. The cylindrical chamber has an axis collinear with the shank axis so that the chamber and shank may rotate as a unit. The invention also includes a flexible, deformable gasket that provides a fluid-tight seal between the shank and the wall of the container. The gasket also provides a fluid-tight seal between the wall of the container and the cylindrical chamber when the shank is advanced sufficiently far into the container that the container and the cylindrical chamber are both engaged by the flexible gasket. The gasket has an enclosure that is adapted to receive and to confine kerf generated during the drilling and tapping of the hole in the container wall.

BRIEF DESCRIPTION OF THE DRAWINGS

The accompanying drawings, which are incorporated in and form a part of the specification, illustrate embodiments of the present invention and, together with the description, serve to explain the principles of the invention.

In the Figures:

FIG. 2 shows a cross-sectional side view of the fluid collecting section of FIG. 1 prior to attachment to the container wall;

FIG. 3 shows a cross-sectional side view of the fluid collecting section of FIG. 1 after affixing it to the container wall;

FIG. 6 shows a cross-sectional side view of an embodiment of the housing of the present invention;

FIG. 7 shows a cross-sectional side view of a housing cap of the present invention;

FIG. 8 shows a cross-sectional side view of an embodiment housing of the present invention;

DETAILED DESCRIPTION OF THE INVENTION

Figure 1:
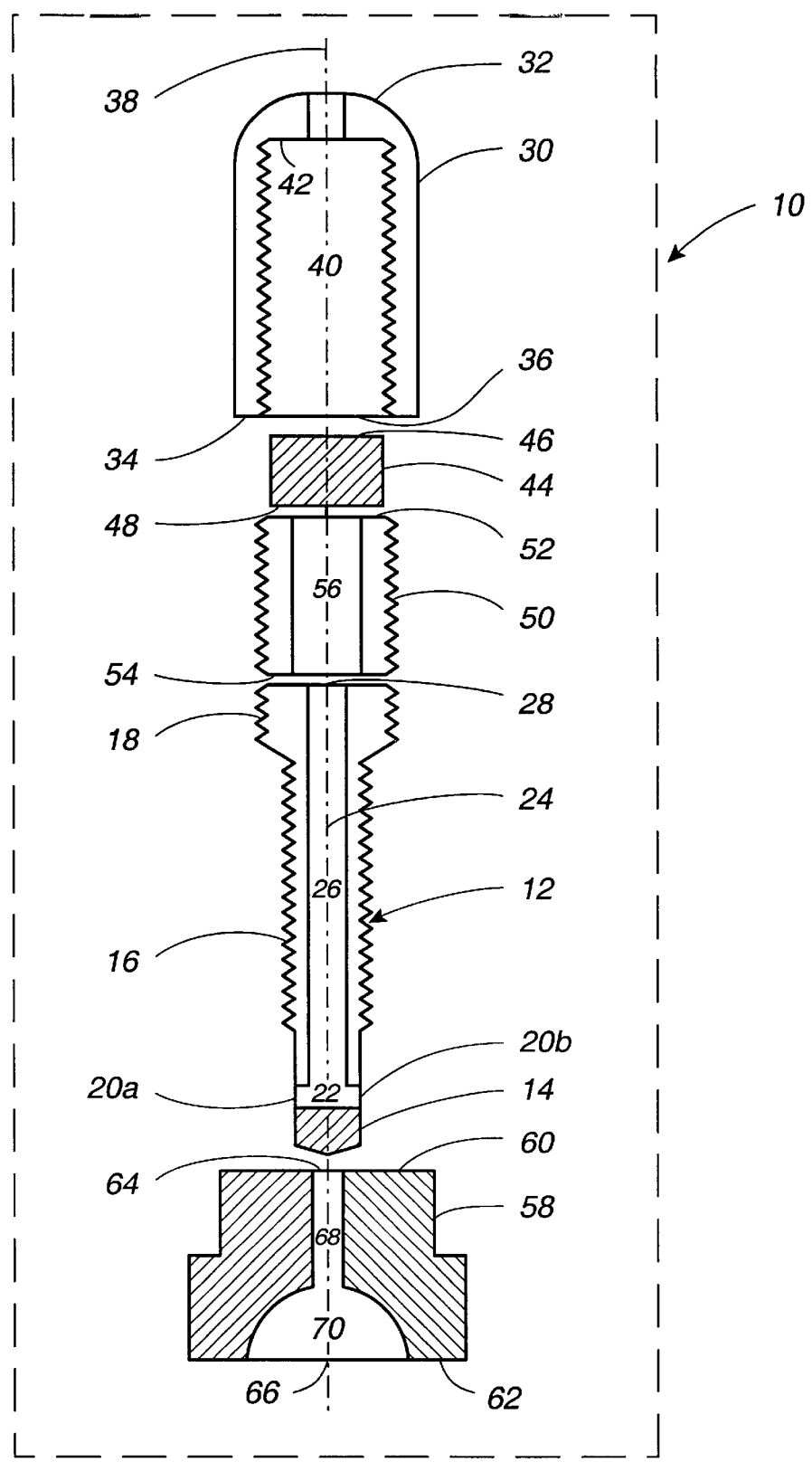
FIG. 1 shows a cross-sectional side view of a fluid collecting section of the present invention.

The present invention includes a tool for extracting and collecting fluid samples from a sealed container. The tool combines a fluid collecting section and a fluid extracting section for obtaining fluid samples. Reference will now be made in detail to the present preferred embodiments of the invention, examples of which are illustrated in the accompanying drawings. Similar or identical structure is identified using identical callouts. Turning now to FIG. 1, an exploded cross-sectional view of the fluid collecting section of an embodiment of the present invention is shown. Fluid collecting section 10 includes a shank 12 having a drilling end 14, a first threaded shank portion 16 adjacent to drilling end 14, and a second threaded shank portion 18 located distally to drilling end 14. Drilling end 14 is configured to drill a hole in a container wall as it is pressed against the wall and rotated. For sufficiently thick walls, first threaded shank portion 16 taps the hole drilled in the container wall. As drilling end 14 is rotated, wall material is cut away to form wall shavings, otherwise known as"kerf,"(not shown). Drilling end 14 may include a single inlet (not shown), or opposing inlets 20a and 20b defining a radial passageway 22 in drilling end 14. Shank 12 has an axis 24 and an internal passageway 26 collinear with axis 24 and extending from radial passageway 22 to opening 28 to provide a channel for fluid.

Fluid collecting section 10 also includes an internally threaded cylindrical housing 30 adapted to fit into the chuck of a rotatable drill such as a hand-held power drill. Housing 30 has a first end 32 and a second end 34. Opening 36 at second end and inlet 38 at first end 32 provide access to passageway 40 of housing 30. Housing 30 is provided with an inner surface 42 near first end 32. Fluid collecting section 10 also includes solid septum 44 having a first surface 46 and a second surface 48. Septum 44 is made of a flexible deformable material such as a neoprene, which is capable of being pierced with a hypodermic needle and forming a fluid-tight seal with the needle, and of self-sealing upon withdrawal of the needle. Septum 44 may also be provided with a teflon coating to enhance the inertness to chemicals by the septum. Fluid collecting section 10 also includes externally threaded cylindrical insert 50 having a first end 52, a second end 54, and an internal axial passageway 56 therethrough to provide a channel for fluid. After septum 44 is placed inside housing 30, insert 50 is screwed into housing 30 until septum 44 is compressed between, and forms a fluid-tight seal with, inner surface 42 of housing 30 and first end 52 of insert 50. Shank 12 is then screwed into housing 30 until it contacts second end 54 of insert 50. Now, a rotation of housing 30 causes shank 12 to rotate with it as a unit.

Fluid collecting section 10 includes gasket 58, which is made of a flexible and deformable material such as neoprene. Gasket 58 has a housing engaging surface 60 and a container sealing surface 62. Gasket 58 has a first opening 64, a second opening 66, and an axial inner passageway 68 therebetween. First opening 64 is much narrower than second opening 66, and widens within gasket 58 to provide a volume 70 for confining wall shavings, i.e. kerf, generated when shank 12 drills a hole into a container wall. Inner passageway 68 has a diameter about one half the diameter of first shank section 16 to allow gasket 58 to mold itself around and form a fluid-tight seal with first threaded shank section 16, and the seal is maintained while shank 12 is drilled into a container wall.

FIG. 2 shows a cross-sectional view of assembled fluid collecting section 10 just prior to drilling into container wall 72. Septum 44 is compressed between insert 50 and inner surface 42 of housing 30. Second shank section 18 is in threaded engagement with housing 30 and is in physical contact with insert 50. If housing 30 is clamped into the chuck of a rotatable drill and rotated, drilling end 14 drills a borehole into the wall while kerf (not shown) is confined within volume 70 of gasket 52. As shank 12 advances into the borehole, so does housing 30 until second end 34 of housing 30 seals against container engaging surface 60 of gasket 58. Operation of the rotatable drill is then discontinued to avoid possible damage to the borehole. Housing 30 is then disengaged from the rotatable power drill, leaving fluid collector section 10 affixed to the container wall. Battery-powered rotatable hand drills that can be used with the present invention often include a stall torque setting that can be adjusted to prevent overdrilling and avoid borehole damage.

FIG. 3 shows fluid collecting section 10 affixed to container wall 72. Housing engaging surface 60 of gasket 58 is compressed against second end 34 of housing 30 to form a fluid-tight seal therewith. Kerf 74 is confined within volume 70 of gasket 58. Gasket 58 is molded around and in fluid-tight engagement with shank 12. Container engaging surface 62 of gasket 58 is in fluid-tight engagement with container wall 72. If the container is filled with a fluid, then shank 12 is now in physical contact with the fluid. A fluid sample may now be extracted from fluid collecting section 10. Since gas, such as atmospheric air, present within collecting section 10 may be confined within after affixing to the wall, a fluid extracting device such as a hypodermic syringe may be used to withdraw the gas prior to extracting a sample of container fluid.

Figures 4, 5:
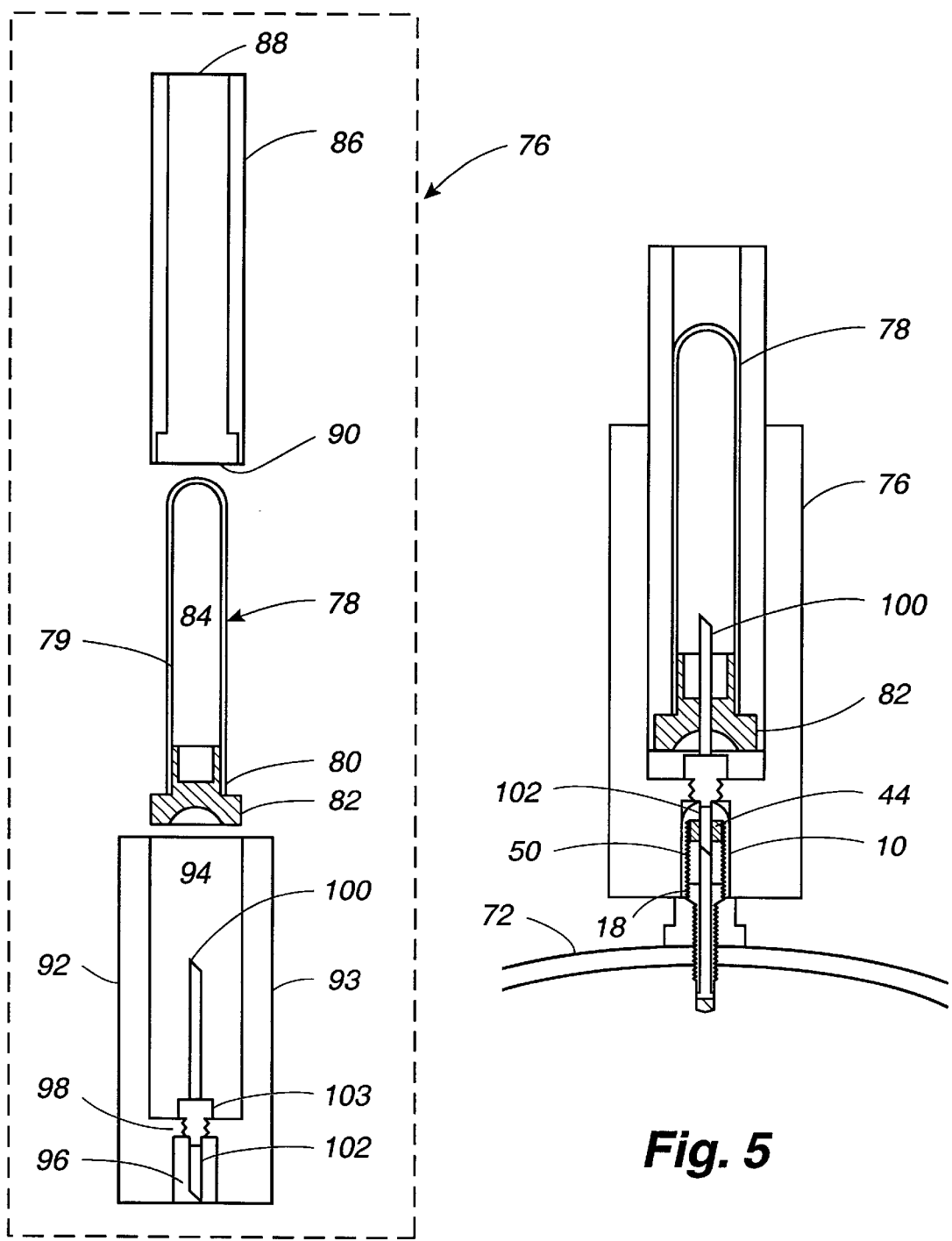
FIG. 4 shows a cross-sectional side view of a sample extracting section of the present invention.
FIG. 5 shows a cross-sectional side view the present invention during the extraction of a fluid sample.

FIG. 4 shows a side view of fluid extracting section 76, which is used to extract fluid from fluid collecting section 10 and protect the user from exposure to fluid. Fluid extracting section 76 includes sample container 78 having a transparent tubular body 79. Open end 80 of body 79 is sealed with a flexible, pierceable plug 82 to form airtight sample chamber 84, which is evacuated, i.e. under at least a partial vacuum, prior to sampling. Fluid extracting section 76 also includes transparent tubular sample container housing 86 having a first open end 88 and a second open end 90 configured to grip plug 82 when container 78 is completely within housing 86. Housing 86 is made of a nonfragile transparent material such as polycarbonate or polystyrene plastic and provides the user with protection from exposure to container fluid and glass pieces if container 78 is a glass container and is damaged during sampling. Fluid extractor section 76 also includes piercing assembly 92 having a transparent tubular body 93 made of a non-fragile material such as polycarbonate or polystyrene plastic and configured to form a pair of axially symmetric enclosures 94 and 96 separated by a partition 98. Enclosure 96 is configured to receive housing 30 of sample collecting section 10. Enclosure 94 is configured to receive sample container housing 86 of fluid collecting section 76. A pair of coaxial hollow piercing members 100 and 102, which are attached axially to partition 98 with piercing member connector 103, provide fluid communication between enclosures 94 and 96. The piercing ends of piercing members 100 and 102 point away from partition 98. In practice, the hollow piercing members are hypodermic needles that are in leakproof engagement with the partition.

FIG. 5 shows a side view of fluid collecting section 10 affixed to container wall 72, and fluid extracting section 76 engaged with fluid collecting section 10. FIG. 5 shows piercing member 100 penetrating plug 82 of sample container 78 and piercing member 102 piercing septum 44 of collecting section 10. The vacuum within sample container 78 draws fluid from within collecting section 10 through piercing members 102 and 100 and into sample container 78. After extracting the fluid sample, the fluid extracting section 76 is removed from fluid collector section 10 by first withdrawing piercing member 102 from septum 44, and then withdrawing piercing member 100 from plug 82 of sample container 78. Multiple fluid samples may be extracted from the affixed collector section 10 by using multiple sample containers 78.

Another embodiment of housing 30 for use with fluid collector section 10 is shown in FIG. 6. Housing 104 has a cylindrical body 106 having a first end 108, a second end 110, and an inner threaded passageway 112 therethrough. A second cylindrical insert 114 having a first end 116, a second end 118, and an inner passageway 120 therethrough is screwed into first end 108 of housing 104. When fluid-collecting section is assembled using housing 104, septum 44 is compressed between first insert 50 and second insert 114.

To provide additional protection against the accidental release of fluid once collecting section 10 is affixed to the container wall, and for providing mechanical protection against an accidental blow, fluid collecting section 10 may be provided with housing cap 122, shown in FIG. 7. Housing cap 122 has a body 124 having a first closed end 126, a second open end 128, an inner threaded portion 130, and an inner surface 132. As shown in FIG. 8, housing 30 of collector section 10 may be provided with an outer threaded portion 134 for threadably engaging cap 122. Second end 128 of cap 122 seals against the container wall 72. Second end 128 may include an adhesive, a flexible deformable material such as neoprene o-ring, or other similar materials to provide a gas-tight seal between cap 122 and container wall 78. Housing 104 may similarly be provided with an outer threaded surface for receiving cap 122.

Figures 9, 10:
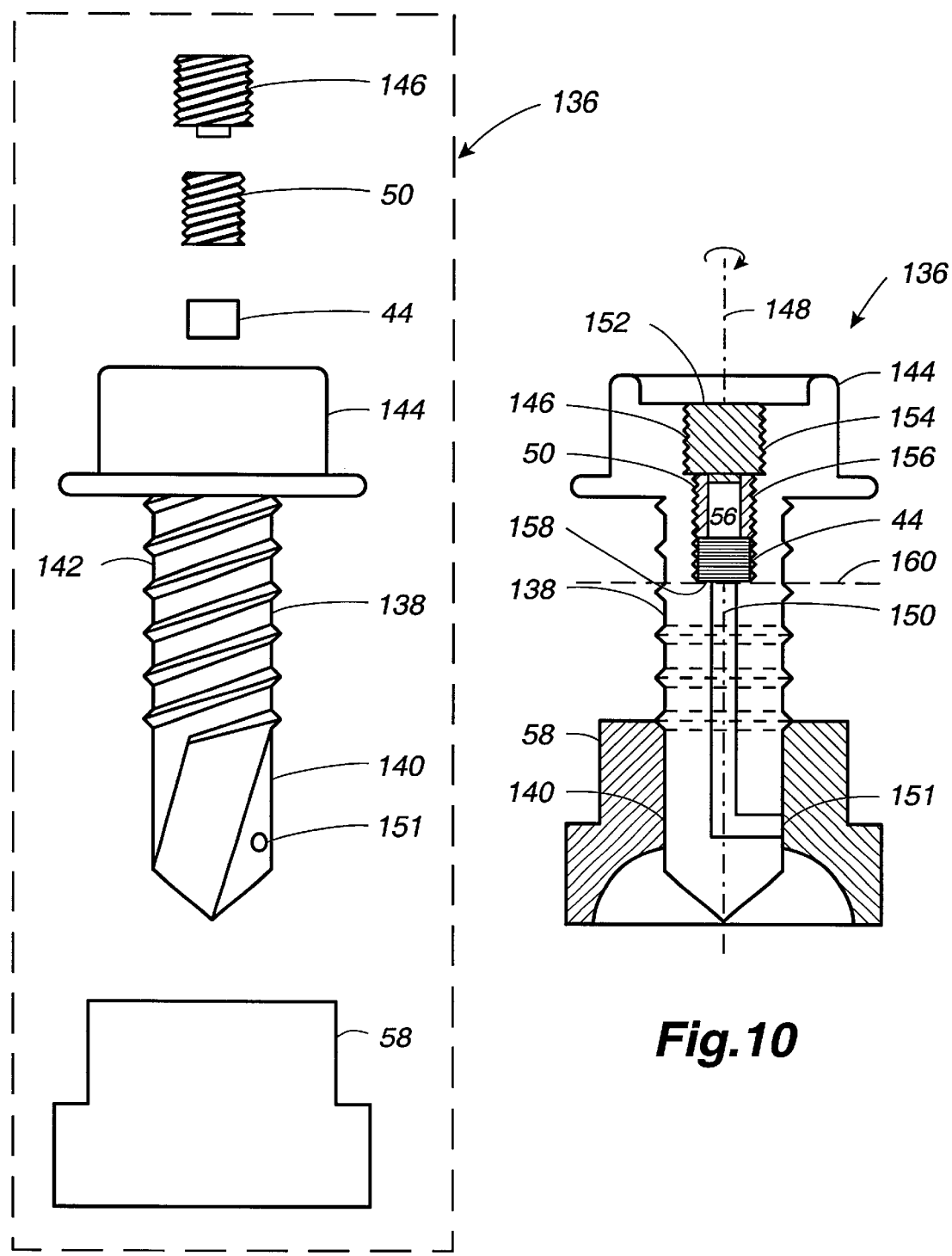
FIG. 9 shows an exploded perspective side view of an embodiment of the fluid collecting section of the present invention.
FIG. 10 shows a cross-sectional side view of the embodiment shown in FIG. 9.

FIG. 9 shows an exploded perspective side view of another embodiment of the fluid collecting section of the present invention. Fluid collecting section 136 includes solid septum 44, externally threaded cylindrical insert 50, and gasket 58 as previously described. Fluid collector section 136 also includes shank 138 having a drilling end portion 140 configured to drill a hole into a container and a threaded shank portion 142 adjacent the drilling end. A head 144 is located adjacent to threaded portion 142 and distally to drilling end 140. Head 144 may be configured to fit into, or engage an attachment that fits into, the chuck of a rotatable drill. For example, head 144 may have a hexagonal shape that would require a rotatable drill attachment for receiving a hexagonal-shaped head. Fluid collector section 136 also includes solid cylindrical threaded insert 146.

FIG. 10 shows a cross-sectional side view of fluid collector 136. Fluid collector section 136 has an axis 148 and a passageway 150 collinear with axis 148 that extends from opening 152 in head 144 to inlet 151 in drilling end 140 of shank 138 to provide a channel for fluid. Widened passageway sections in passageway 150 are defined by a first threaded portion 154 in head 144, a second threaded portion 156 extending from first threaded portion 154 and into shank 138, and an inner annular flat surface 158 having a surface plane 160 perpendicular to axis 148 of collector section 136. Fluid collector section 136 is assembled by first inserting septum 44 through opening 152 until it rests on flat surface 158, then threadably engaging insert 50 with second threaded portion 156 of passageway 150 such that it compresses into and seals against septum 44, and then screwing solid insert 146 into first threaded portion 154 of passageway 150. After affixing fluid collecting section 136 to a container wall, solid insert 146 is removed so that septum 44 is accessible via passageway 56 of insert 50 for piercing by the fluid extractor.

Figure 11:
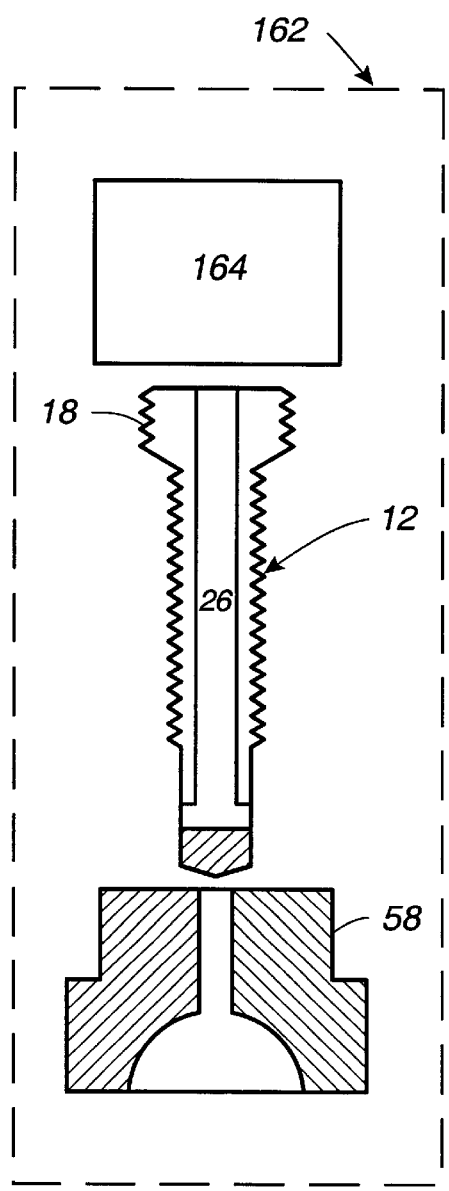
FIG. 11 shows an exploded cross-sectional side view of an embodiment of the fluid collecting section of the present invention.

A cross-sectional side view of another embodiment of the fluid collecting section of the present invention is shown in FIG. 11. Fluid collecting section 162 includes gasket 58, shank 12, and valve assembly 164 attached to second threaded shank portion 18 of shank 12. Valve assembly 164, which controls the flow of fluid through passageway 26 and out of shank 12, may include the valve described in the '140 patent to Clark, the valve in the '383 patent to Kammerad, or any similar valve and a means for connecting the valve to shank 12.

Figure 12:
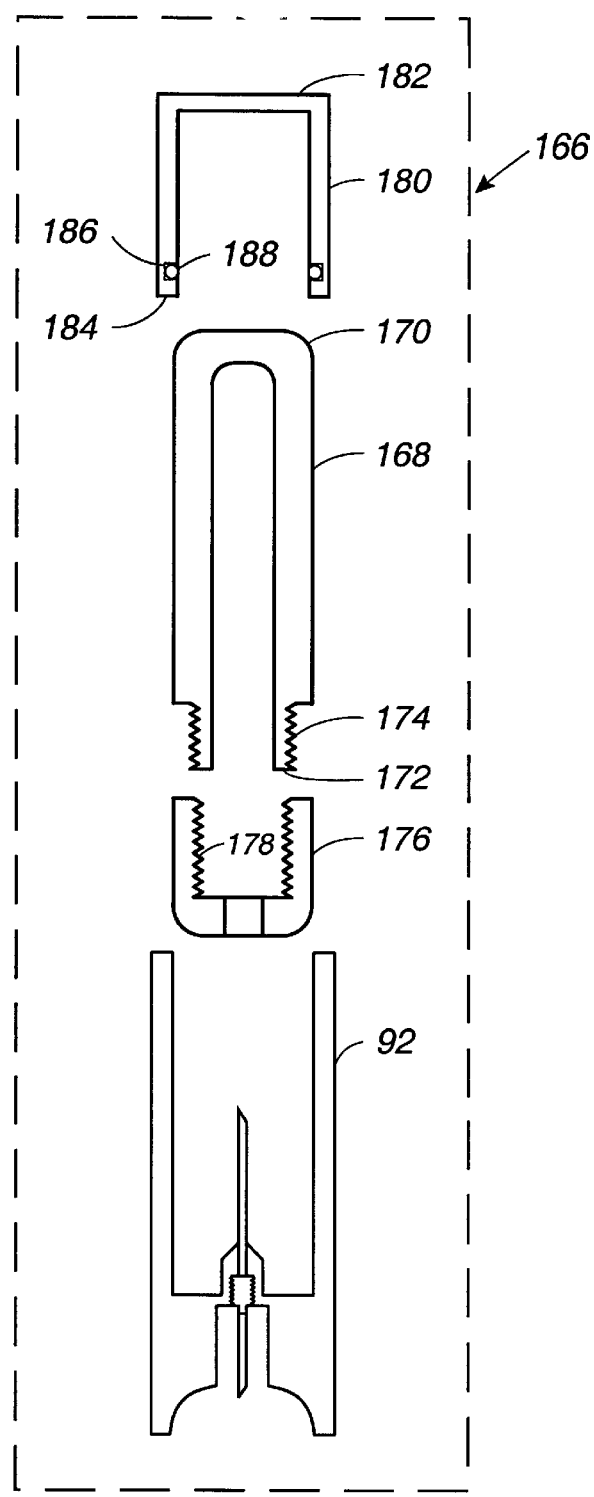
FIG. 12 shows an exploded cross-sectional side view of an embodiment of the fluid extractor section of the present invention.

An exploded cross-sectional side view of a second embodiment of the fluid extractor section of the present invention is shown in FIG. 12. Fluid extractor 166 includes piercing assembly 92, and sample container 78 as shown in FIG. 4. Fluid extractor 166 also includes sample container housing 168 having a closed end 170, an open end 172, and an externally threaded portion 174 near the open end 172. Fluid extractor 166 also includes a housing cap 176 having an internally threaded surface 178 for threadably engaging threaded portion 174 of housing 168. To provide additional protection against accidental exposure to fluid, fluid extractor 166 also includes housing cover 180 having a closed end 182, an open end 184, circumferential slot 186, and o-ring 188 which fits into slot 186. After obtaining a fluid sample, housing 168 (with threadably attached cap 176) is inserted into open end 184 of housing cover 180. O-ring 188 of cover 180 seals against housing 168.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A rotatable tool for collecting fluid through the wall of a container, comprising in combination:

(a) a cylindrical shank having a portion at one end thereof adapted for drilling a hole in the container wall and a threaded portion for tapping the hole in the container wall drilled by the drilling portion and for advancing said shank into the container when said shank is rotated, said shank further having an axis and an inner passageway along the axis in communication with at least one radial inlet hole in the drilling portion and opening at the end of said shank opposite the drilling section, the at least one radial inlet and the passageway being adapted to receive fluid from the container;

(b) a cylindrical chamber affixed to the end of said shank opposite to the drilling portion thereof for receiving and storing fluid passing through the passageway, said cylindrical chamber having an axis and being disposed such that the axis of said cylindrical chamber is collinear with the axis of said shank and said shank and said cylindrical chamber are rotated as a unit; and (c) a flexible deformable gasket for providing a fluid-tight seal between said shank and the wall of the container, and for providing a fluid-tight seal between the wall of the container and said cylindrical chamber when said shank is advanced sufficiently far into the container that the container and said cylindrical chamber are both engaged by said flexible gasket, said gasket having a volume being adapted to receive and to confine kerf generated during the drilling of the hole into the container wall and during the tapping thereof.

2. The tool of claim 1, further including extracting means for extracting and containing fluid from said cylindrical chamber.

3. The tool of claim 1, wherein said cylindrical chamber comprises a pierceable resealable septum for extracting fluid therethrough.

4. The tool of claim 1, wherein said cylindrical chamber comprises a fluid valve means for extracting fluid therethrough.

5. The tool of claim 3, wherein said extracting means comprises a hypodermic syringe for piercing said septum and extracting fluid from said cylindrical chamber.

6. The tool of claim 5, wherein said cylindrical chamber is adapted to be received by a chuck of a hand drill, whereby said cylindrical chamber is rotated about the axis thereof.

7. The tool of claim 3, wherein said extracting means comprises an evacuated receptacle having a resealable septum for introducing and extracting fluids therefrom.

8. The tool of claim 7, further including a hollow tube having two ends and sharpened points at both ends thereof, one sharpened end for piercing said septum of said cylindrical chamber and the other sharpened end for subsequently piercing said septum of said receptacle, whereby fluid is withdrawn from said cylindrical chamber and transferred to said receptacle.

* * * * *